United States Patent
Orme et al.

(10) Patent No.: US 6,960,587 B2
(45) Date of Patent: Nov. 1, 2005

(54) CONDENSED PYRAZINDIONE DERIVATIVES AS PDE INHIBITORS

(75) Inventors: Mark W. Orme, Seattle, WA (US); Lisa M. Schultze, Woodinville, WA (US); Jason Scott Sawyer, Indianapolis, IN (US)

(73) Assignee: Lilly Icos LLC, Wilmington, DE (US)

( * ) Notice: Subject to any disclaimer, the term of this patent is extended or adjusted under 35 U.S.C. 154(b) by 293 days.

(21) Appl. No.: 10/398,819
(22) PCT Filed: Oct. 9, 2001
(86) PCT No.: PCT/US01/31386
§ 371 (c)(1), (2), (4) Date: Apr. 9, 2003
(87) PCT Pub. No.: WO02/38563
PCT Pub. Date: May 16, 2002

(65) Prior Publication Data
US 2004/0038978 A1 Feb. 26, 2004

Related U.S. Application Data
(60) Provisional application No. 60/246,805, filed on Nov. 8, 2000.

(51) Int. Cl.$^7$ .................. C07D 471/14; C07D 487/14; C07D 491/14; A61K 31/4995; A61P 9/00
(52) U.S. Cl. .................. 514/250; 544/344; 544/345
(58) Field of Search ................ 544/344, 345; 514/250

(56) References Cited

FOREIGN PATENT DOCUMENTS

| WO | WO 97/03675 | 2/1997 |
| WO | WO 97/03985 | 2/1997 |

OTHER PUBLICATIONS

Lucas et al. Pharmacological Reviews 52 (3), 375–413, 2000.*
West, Anthony R., Solid State Chemistry and its Applications, Wiley, New York, 1988, pp. 358 & 365.*

* cited by examiner

Primary Examiner—Venkataraman Balasubramanian
(74) Attorney, Agent, or Firm—Marshall, Gerstein & Borun LLP

(57) ABSTRACT

Compounds of the general structural formula (I), and use of the compounds and salts and solvates thereof, as therapeutic agents.

20 Claims, No Drawings

CONDENSED PYRAZINDIONE DERIVATIVES AS PDE INHIBITORS

CROSS REFERENCE TO RELATED APPLICATION

This is the U.S. national phase application of International Application No. PCT/US01/31386, filed Oct. 9, 2001, which claims the benefit of U.S. provisional patent application Ser. No. 60/246,805, filed Nov. 8, 2000.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

DETAILED DESCRIPTION OF THE INVENTION

The present invention provides compounds of formula (I)

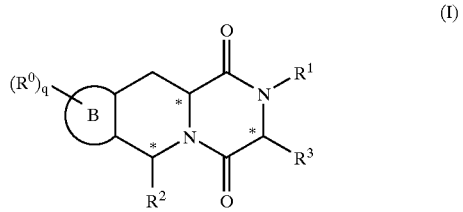

(I)

wherein $R^0$, independently, is selected from the group consisting of halo, $C_{1-6}$alkyl, $C_{2-6}$alkenyl, aryl, heteroaryl, $C_{3-8}$cycloalkyl, $C_{3-8}$heterocycloalkyl, $C_{1-3}$-alkylenearyl, $C_{1-3}$alkyleneheteroaryl, Het, $C(=O)R^a$, $OC(=O)OR^a$, $C_{1-4}$alkyleneNR$^a$R$^b$, $C_{1-4}$alkyleneHet, $C_{1-4}$alkyleneC(=O)OR$^a$, $C(=O)NR^a SO_2 R^b$, $C(=O)C_{1-4}$alkyleneHet, $C(=O)NR^a C_{3-4}$alkyleneOR$^b$, $C(=O)NR^a C_{1-4}$alkyleneHet, $OR^a$, $OC_{1-4}$alkyleneC(=O)OR$^a$, $OC_{1-4}$alkyleneNR$^a$R$^b$, $OC_{1-4}$alkyleneHet, $OC_{1-4}$alkyleneOR$^a$, $OC_{1-4}$alkyleneNR$^a$C(=O)OR$^b$, $NR^a R^b$, $NR^a C_{1-4}$alkyleneNR$^a$R$^b$, $NR^a C(=O)R^b$, $NR^a C(=O)NR^a R^b$, $N(SO_2 C_{1-4}alkyl)_2$, $NR^a(SO_2 C_{1-4}alkyl)$, nitro, trifluoromethyl, trifluoromethoxy, cyano, $SO_2 NR^a R^b$, $SO_2 R^a$, $SOR^a$, $SR^a$, and $OSO_2 CF_3$;

$R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl $C_{1-3}$alkyl, and heteroaryl$C_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

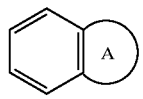

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is hydrogen or $C_{1-6}$alkyl, or $R^1$ and $R^3$ together form a 3- or 4-membered alkyl or alkenyl chain component of a 5- or 6-membered ring;

fused ring B is a 5-, 6-, or 7-membered ring, saturated or partially or fully unsaturated, comprising carbon atoms and optionally one to three heteroatoms selected from oxygen, sulfur, and nitrogen;

$R^a$ is selected from the group consisting of hydrogen, $C_{1-10}$alkyl, $C_{2-10}$alkenyl, $C_{2-10}$alkynyl, aryl, heteroaryl, aryl$C_{1-3}$alkyl, $C_{1-3}$alkylenearyl, $C(=O)OR^b$, $C(=O)N(R^b)_2$, $C_{1-4}$alkyleneN(R$^b)_2$, $CF_3$, $OCF_3$, $OR^b$, $OC(=O)-R^b$, $OC_{1-4}$alkyleneC(=O)OR$^b$, $C_{1-4}$alkyleneOC$_{1-4}$alkyleneC(=O)OR$^b$, $C(=O)NR^b SO_2 R^b$, $C(=O)C_{1-4}$alkyleneHet, $C_{2-6}$alkenyleneN(R$^b)_2$, $C(=O)NR^b C_{1-4}$alkyleneOR$^b$, $C(=O)NR^b C_{1-4}$alkyleneHet, $OC_{2-4}$alkyleneN(R$^b)_2$, $OC_{1-4}$alkyleneCH(OR$^b$)—CH$_2$N(R$^b)_2$, $OC_{2-4}$alkyleneOR$^b$, $OC_{2-4}$alkyleneNR$^b$C(=O)OR$^b$, $N(R^b)_2$, $NR^b C_{1-4}$alkyleneN(R$^b)_2$, $NR^b C(=O)R^b$, $NR^b C(=O)-N(R^b)_2$, $N(SO_2 C_{1-4}alkyl)_2$, $NR^b(SO_2 C_{1-4}alkyl)$, $SO_2 N(R^b)_2$, $OSO_2$trifluoromethyl, $C(=O)R^b$, $C_{1-3}$alkyleneOR$^b$, $CN$, and $C_{1-6}$alkyleneC(=O)OR$^b$;

$R^b$ is selected from the group consisting of hydrogen, $C_{1-6}$alkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

q is 0, 1, 2, 3, or 4; and pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl.

The terms "alkenyl" and "alkynyl" are defined identically as "alkyl," except for containing a carbon-carbon double bond or carbon-carbon triple bond, respectively. "Cycloalkenyl", is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl", is defined herein as an alkyl group substituted with one or more halo substituents, independently selected from fluoro, chloro, bromo, and iodo. Similarly, "halocycloalkyl", is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl", and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxyl" is defined as —OH.

The term "alkoxyl" is defined as —OR, wherein R is alkyl.

The term "alkoxyalkyl" is defined as an alkyl group wherein a hydrogen atom has been replaced by an alkoxy group. The term "(alkylthio)-alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl", is defined as —CF$_3$.

The term "trifluoromethoxyl" is defined as —OCF$_3$.

The term "cyano" is defined as —CN.

Substituents $R^0$ can be positioned on a carbon atom or a heteroatom of ring B. In preferred embodiments, q is 0, or $R^0$ is selected from the group consisting of $C_{1-6}$alkyl, aryl, $C_{1-3}$alkylenearyl, $C_{1-3}$alkyleneheteroaryl, Het, OR$^a$, C(=O) OR$^a$, $C_{1-4}$alkylene-NR$^a$R$^b$, C(=O)R$^a$, NR$^a$R$^b$, $C_{3-8}$cycloalkyl, and C(=O)NR$^a$R$^b$.

In other preferred embodiments, $R^1$ is selected from the group consisting of hydrogen, $C_{1-6}$alkyl, halo$C_{1-6}$alkyl, $C_{3-8}$cycloalkyl, $C_{3-8}$cycloalkylene$C_{1-3}$alkyl, aryl$C_{2-3}$alkyl, and heteroaryl$C_{1-3}$alkyl.

In a preferred group of compounds of formula (I), $R^2$ is represented by

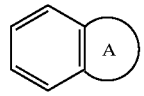

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

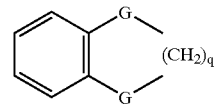

wherein q is an integer 1 or 2, and G, independently, is $C(R^a)_2$, O, S, or NR$^a$. The bicyclic ring comprising the $R^1$ substituent typically is attached to the rest of the molecule by a phenyl ring carbon atom.

In an especially preferred group of compounds of formula (I), $R^2$ is represented by an optionally substituted bicyclic ring

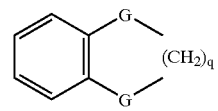

wherein q is 1 or 2, and G, independently, are CH$_2$ or O. Especially preferred $R^2$ substituents include

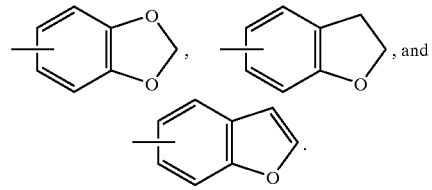

Within this particular group of compounds, nonlimiting examples of substituents for the bicyclic ring include halogen (e.g., chlorine), $C_{1-3}$alkyl (e.g., methyl, ethyl, or i-propyl), OR$^a$ (e.g., methoxy, ethoxy, or hydroxy), $CO_2R^a$, halomethyl or halomethoxy (e.g., trifluoromethyl or trifluoromethoxy), cyano, nitro, and NR$^a$R$^b$.

Examples of ring B include, but are not limited to the following, including residues thereof:

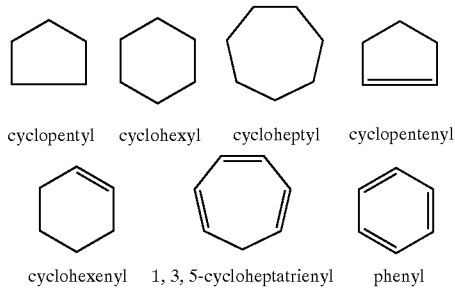

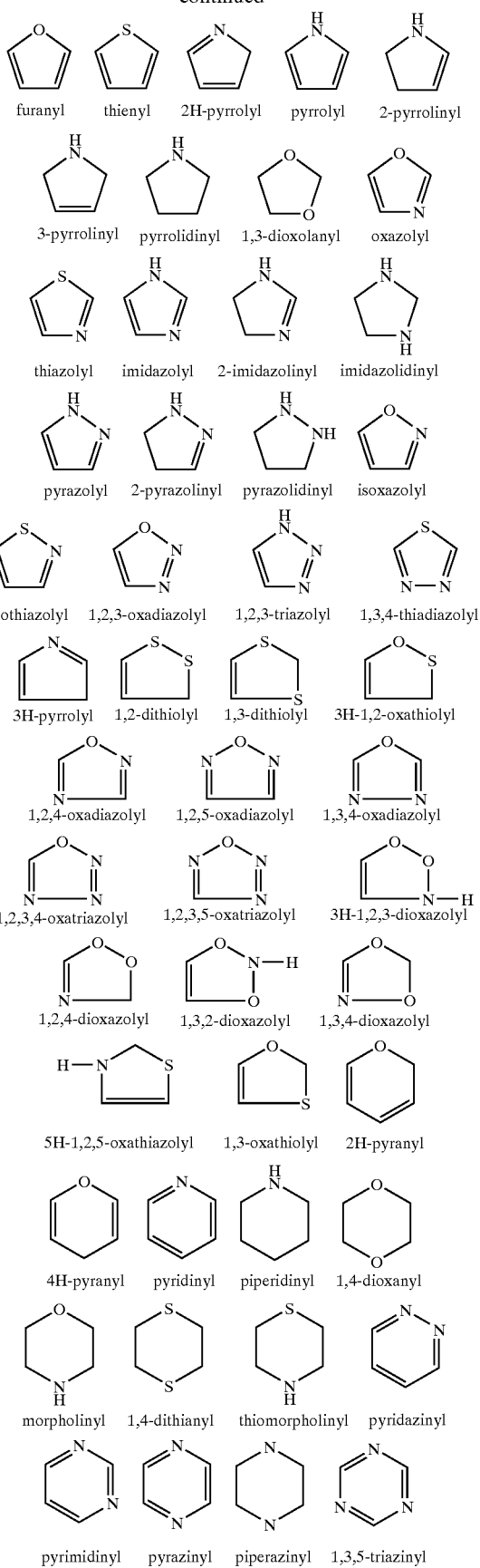
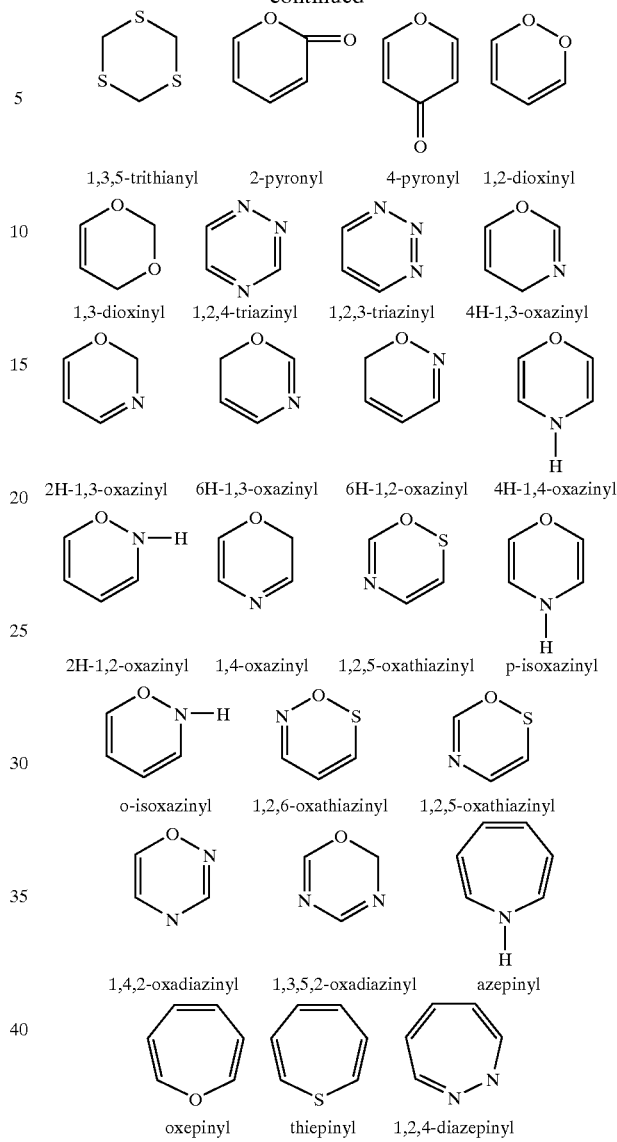

The R⁰ substituents can be bound to a carbon or a nitrogen atom of the B ring.

An especially preferred subclass of compounds within the general scope of formula (I) is represented by compounds of formula (II)

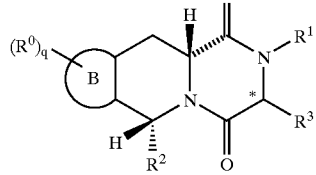

(II)

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed-as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula, (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose., or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the-present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, and $R^3$ are as defined in structural formula (I) above. Generally, compounds of structural formula (I) can be prepared according to the following synthetic schemes.

In particular, using an appropriately substituted 2-arylethylamine or 2-heteroarylethylamine, a compound of general structural formula (I) can be prepared using the methods outlined below. Methods A–C are examples of synthetic routes to the diketopiperazine-tetrahydroisoquinolines and diketopiperazine-tetrahydroimidazopyridines of formula (I). However, additional synthetic routes exist for the synthesis of tetrahydroisoquinolines. For example, see, M. D. Rozwadowska, *Heterocycles,* 39, 903 (1994); M. Shamma, *Isoquinoline Alkaloinds, Chemistry and Pharmacology,* Academis Press: New York (1972); and T. Kametani, *The Chemistry of the Isoquinoline Alkaloids,* Elsevier, Amsterdam (1969).

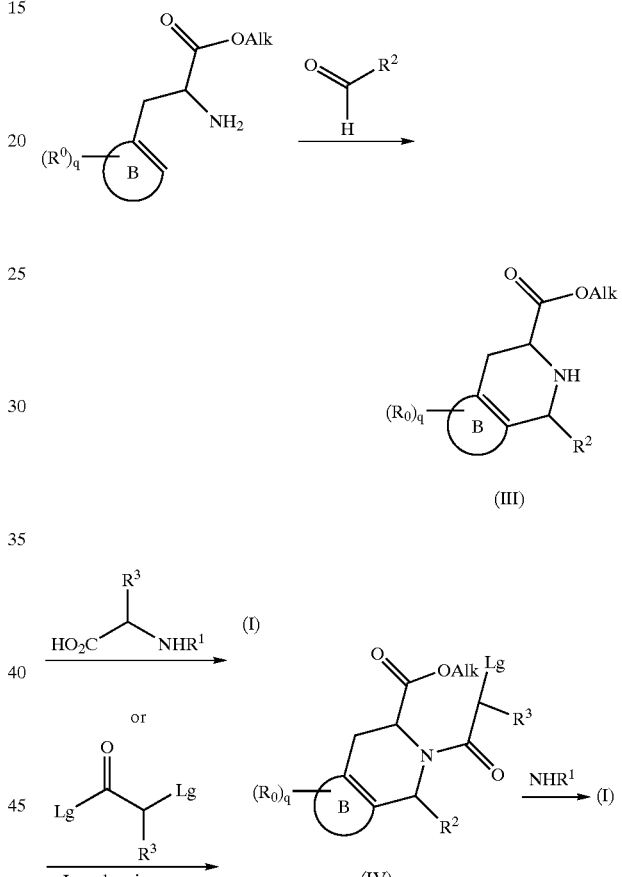

The compounds of general structural formula (III) can be prepared, for example, by the Pictet-Spengler reaction. See, W. Whaley et al., *Org. React,* 6, 151–206 (1951); S. M. Hutchins et al., *Tetrahedon Lett.,* 37, 4865 (1996); R. D. Cox et al., *Chem. Rev.,* 95, 1797 (1995); and A. Yokoyama et al., *J. Org. Chem.,* 64, 611 (1999). A substituted arylethylamine or heteroarylethylamine ester is reacted with an aldehyde to provide a compound (III). The resulting secondary amine (III) then is treated with either an amino acid or an acid halide under suitable acylation conditions to form an amide-ester. Ring cyclization to form a compound of structural formula (I) is accomplished by an intramolecular amine attack on the ester. Compounds (I) also can be derived from a suitable side chain bearing a leaving group (e.g., compound (IV)) that reacts with a primary amine.

GENERAL METHOD B

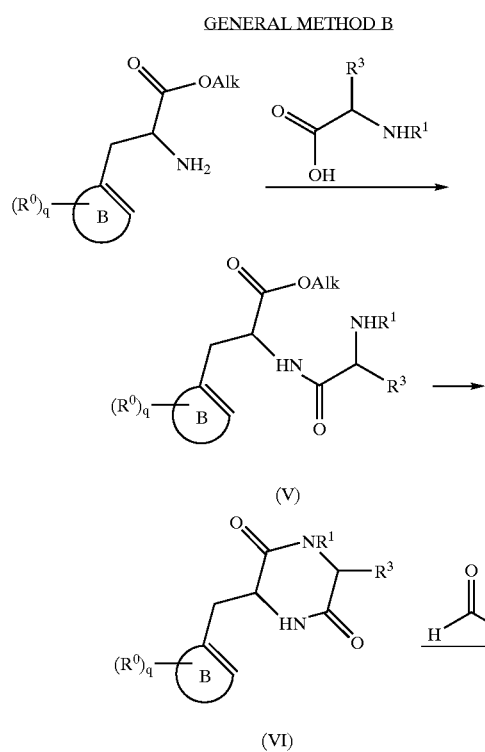

Alternatively, a compound (I) can be prepared by first reacting an arylethylamine or heteroarylethylamine with an amino acid under typical peptide coupling conditions to form an amide (V). Ring cyclization to form a diketopiperazine (VI) is accomplished by intramolecular amine attack on the ester. The resulting piperazine (VI) is subjected to a condensation reaction with an aldehyde under modified Pictet-Spengler conditions to provide a compound of structural formula (I). For a discussion of the modified Pictet-Spengler reaction, see T. A. Miller et al., *Bioorg. Med. Chem. Lett.*, 8, 1065 (1998); A. Previero et al., *Canadian J. of Chemistry*, 46, 3404 (1968); and P. Ducrot et al., *Tet. Lett.*, 40, 9037 (1999).

GENERAL METHOD C

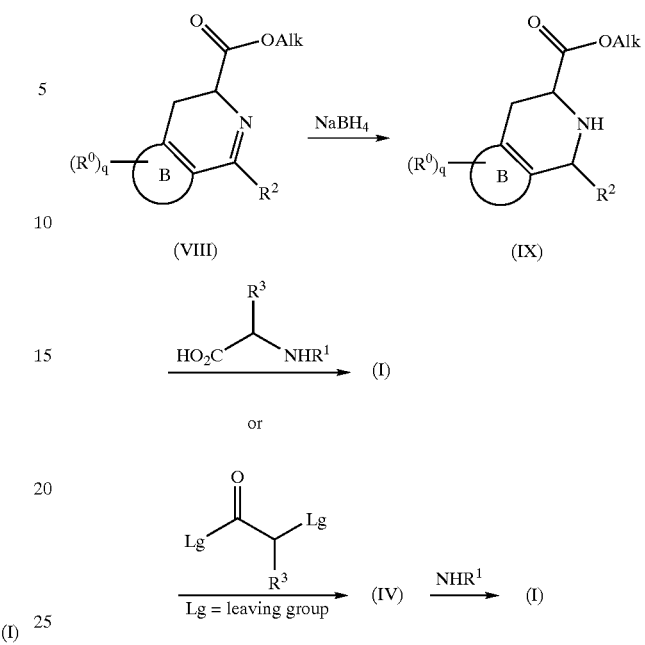

A tetrahydroisoquinoline skeleton also can be constructed using the Bischler-Napieralski reaction, which includes a cyclodehydration of an acylated β-arylethylamine. $P_2O_5$ or $POCl_3$ are the most typical cyclization reagents. See, W. M. Whaley et al., *Org. React, VI,* 74–150 (1951); W. D. F. Meutermans et al., *Tetrahedron Lett.*, 36, 7709 (1995); A. Ishida et al., *Chem. Pharm. Bull.*, 34, 1995 (1986); and A. K. Saxena et al., *Indian J. Chem.*, 13, 230 (1975). Reduction of the resulting imine (VIII), with $NaBH_4$, for example, provides a 1,2,3,4-tetrahydro-β-carboline (IX).

A modified method C avoids racemisation because the amine first is acylated, then converted to the thioamide, for example, with Lawesson's reagent. Treatment of the thioamide with an alkyl halide or acyl halide provides an iminium halide (XI). Reduction of the crude intermediate (XII) with $NaBH_4$ at reduced temperature stereoselectively leads to the tetrahydroisoquinoline (IX).

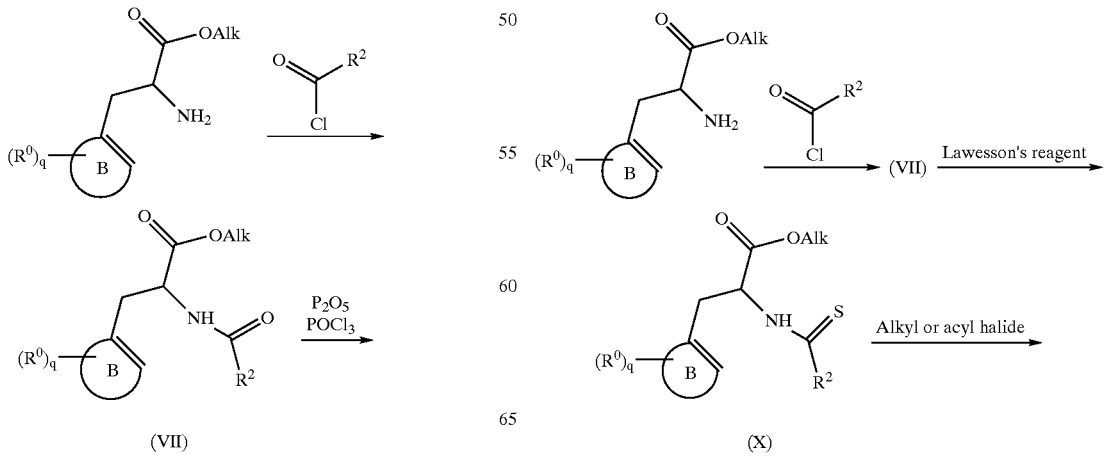

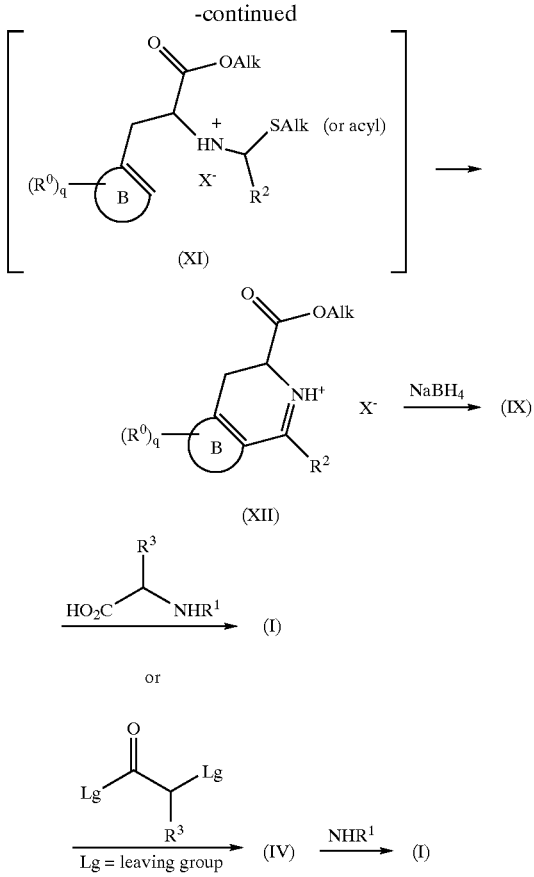

In the synthesis of compounds of structural formula (I), protecting compounds and protecting groups, like benzyl chloroformate and trichloroethyl chloroformate, which are well known to persons skilled in the art, can be used. Such protecting groups are disclosed, for example, in T. W. Greene et al. "Protective Groups in Organic Synthesis, Third Edition," John Wiley and Sons, Inc., NY, N.Y. (1999). These protecting groups are removed in the final steps of the synthesis under basic, acidic, or hydrogenolytic conditions which are readily apparent to those skilled in the art. By employing appropriate starting materials, and manipulation and protection of chemical functionalities, synthesis of compounds of structural formula (I) not specifically set forth herein can be accomplished by methods analogous to the schemes set forth above.

Compounds of formula (I) can be converted to other compounds of formula (I). Thus, for example, when a compound contains a substituted aromatic ring, it is possible to prepare another suitably substituted compound of formula (I). Examples of appropriate interconversions include, but are not limited to, $OR^b$ to hydroxy by suitable means (e.g., using an agent such as $BBr_3$, $SnCl_2$, or a palladium catalyst, such as palladium-on-carbon), or amino to substituted amino, such as alkylamine, using standard acylating or sulfonylating conditions.

Compounds of formula (I) can be prepared by the method above as individual stereoisomers or as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by.(i) salt formation, or (ii) solvate (e.g., hydrate) formation.

The following abbreviations are used hereafter in the accompanying examples: rt (room temperature), min (minute), h (hour), g (gram), mmol (millimole), m.p. (melting point), eq (equivalents), L (liter), mL (milliliter), $\mu$L (microliters), $Et_2O$ (diethyl ether), $CH_2Cl_2$ (dichloromethane), MeOH (methanol), $Et_3N$ (triethylamine), EtOAc (ethyl acetate), AcOH (acetic acid), HCl (hydrochloric acid), $MeNH_2$ (methylamine), TFA (trifluoroacetic acid), IPA (isopropyl alcohol), aq (aqueous), NaCl (sodium chloride), $Na_2SO_4$ (sodium sulfate), $NaHCO_3$ (sodium bicarbonate), and THF (tetrahydrofuran).

The following illustrates specific examples of compounds of structural formula (I) and synthetic routes to compounds (I).

PREPARATION OF EXAMPLE 1

(+−, cis)-4-Benzo[1,3]dioxol-5-yl-7-methyl-3,4,6,7,8a,9-hexahydro-1,3,4a,7-tetraaza-cyclopenta[b]naphthalene-5,8-dione hydrochloride

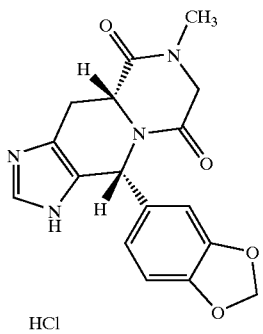

Example 1 was prepared from D-histidine monohydrochloride monohydrate by the following synthetic scheme. Also see S. M. Hutchins et al., *Tet. Letters*, 37, 4865–4868 (1996).

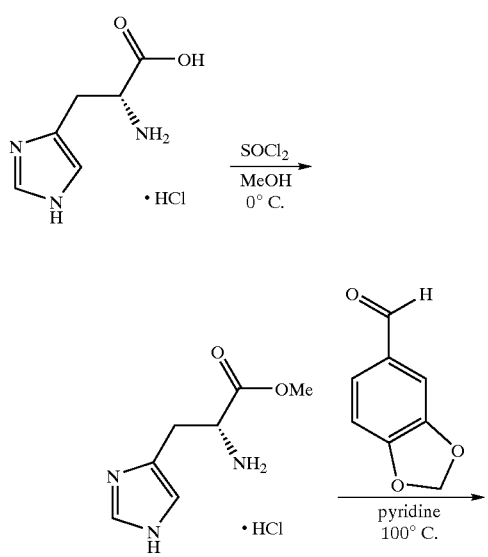

Intermediate 1

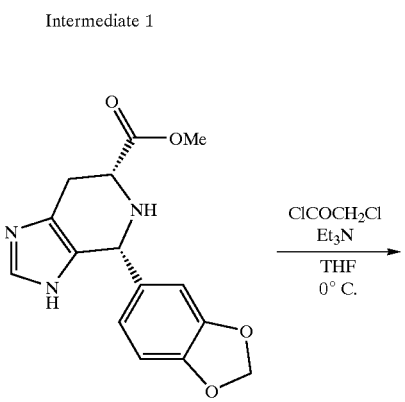

Intermediate 2

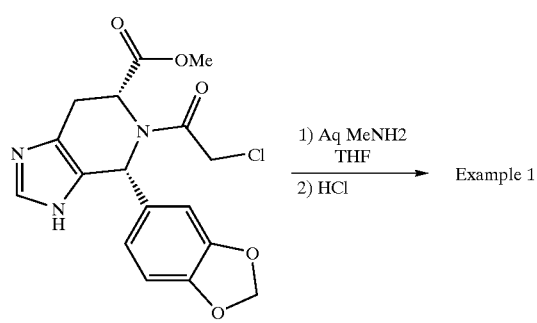

Example 1

Preparation of D-Histidine Methyl Ester Monohydrochloride (Intermediate 1)

Thionyl chloride (29.37 g, 18.0 mL, 246.9 mmol) was added dropwise to a suspension of D-histidine monohydrochloride monohydrate (10.35 g, 49.37 mmol) in anhydrous MeOH (150 mL) at 0° C. under a nitrogen blanket. The resulting mixture was slowly warmed to room temperature, then stirred for 24 hours. The solvent then was removed under reduced pressure to provide a white solid. The residue was suspended in Et$_2$O, which was collected by filtration. Analysis of the resulting solid by $^1$H NMR showed it to be a mixture of starting material and Intermediate 1. The thionyl chloride treatment was repeated three times as described above to yield a white solid (11.74 g, 100%) with less than 10% starting material present: $^1$H NMR (300 MHz, CDCl$_3$): δ 9.07 (d, J=1.2 Hz, 1H), 8.7–9.1 (bs, 1H), 7.52 (s, 1H), 4.47 (t, J=7.1 Hz, 1H), 3.73 (s, 3H), 3.32–3.29 (m, 2H).

Preparation of (+/−)-cis-β-carboline (Intermediate 2)

A suspension of Intermediate 1 (3.24 g, 14.59 mmol) and piperonal (2.63 g, 17.51 mmol) in pyridine (70 mL) was warmed to 100° C., then stirred for 4 hours under a nitrogen blanket. The resulting orange solution was cooled to room temperature and concentrated in vacuo. The crude product was purified by column chromatography (silica gel, 0–20% MeOH/CH$_2$Cl$_2$) to yield 1.72 g (39.2%) of an orange solid: TLC R$_f$ (10% MeOH/CH$_2$Cl$_2$)=0.39; $^1$H NMR (300 MHz, CDCl$_3$): δ 8.99 (s, 1H), 7.07 (s, 1H), 7.03 (s, 2H), 6.09 (s, 2H), 5.71 (s, 1H), 4.70–4.65 (m, 1H), 3.80 (s, 3H), 3.36–3.25 (m, 2H) MS (API) m/z 302 (M+H). The trans carboline was also eluted from the column, but not in pure form: TLC R$_f$ (0.10% MeOH/—CH$_2$Cl$_2$)=0.34.

Preparation of (+/−)-cis-2-chloroacetyl-β-carboline (Intermediate 3)

Chloroacetyl chloride (0.6 mL, 7.4 mmol) was added dropwise to a mixture of Intermediate 2 (1.72 g, 5.7 mmol) and Et$_3$N (1.6 mL, 11.4 mmol) in THF (40 mL) and water (5 mL) at 0° C. under a nitrogen blanket. The resulting mixture was warmed to room temperature, then stirred for about 1 hour. The reaction was quenched with 1N HCl (2 mL), then concentrated in vacuo. The crude product was purified by column chromatography (silica gel, 5–10% MeOH/—CH$_2$Cl$_2$) to provide 0.49 g (22.8%) of a light yellow solid: TLC R$_f$ (3% EtOAc/CH$_2$Cl$_2$)=0.43; MS (API) m/z 378 (M+H)

PREPARATION OF EXAMPLE 1

A mixture of crude Intermediate 3 (0.49 g, 1.29 mmol), 40% MeNH$_2$ in water (1.10 mL, 6.48 mmol) in THF (20 mL) was heated at 45° C. under a nitrogen blanket for 45 minutes. The reaciton was incomplete. Water (2 mL) was added to give a clear two-phase mixture. After an additional 20 minutes, the resulting solution was cooled to room temperature, quenched with concentrated HCl (4 mL), and concentrated to remove THF. The resulting slurry was filtered, and the solid was washed forward with water and acetone. The product was obtained as a white solid (0.16 g, 36%) after drying at 45° C. under vacuum: mp 227–230° C.; TLC R$_f$ (10% MeOH/CH$_2$Cl$_2$)=0.20; $^1$H NMR (300 MHz, DMSO-d$_6$): δ 14.7 (bs, 2H), 8.94 (s, 1H), 6.80–6.91 (m, 3H), 6.00 (s, 1H), 5.96 (s, 2H), 4.35 (dd, J=4.3 Hz, J=11.2 Hz, 1H), 4.13 (d, J=17.1 Hz, 1H), 3.97 (d, J=17.6 Hz, 1H), 3.60 (bs, 1H), 3.41 (dd, J=4.6 Hz, J=16.4 Hz, 1H), 3.17–3.27 (m, 1H), 2.90 (s, 3H); MS (API) m/z 341 (M+H); [α]$_D^{25° C.}$=no observed rotation (c=0.15, DMSO). Anal. Calcd for C$_{17}$H$_{17}$N$_4$O$_4$.HCl.0.4H$_2$O: C, 53.17; H, 4.67; N, 14.59. Found: C, 53.26; H, 4.54; N, 14.52. The relative stereochemistry of the product was confirmed to be the cis isomer by NOE difference experiments (DMSO-d$_6$): positive NOE enhancements from the C12a proton at 4.35 ppm to the C$_4$ proton at 6.00 ppm.

PREPARATION OF EXAMPLE 2

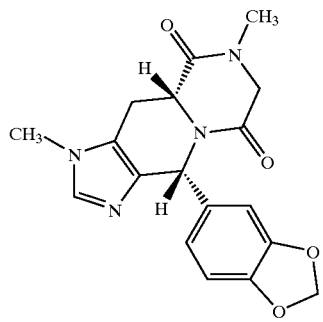

The compound of Example 2 can be prepared in a manner similar to Example 1:

PREPARATION OF EXAMPLE 3

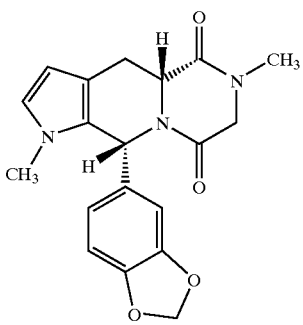

The compound of Example 3 can be prepared by the following synthetic sequence.

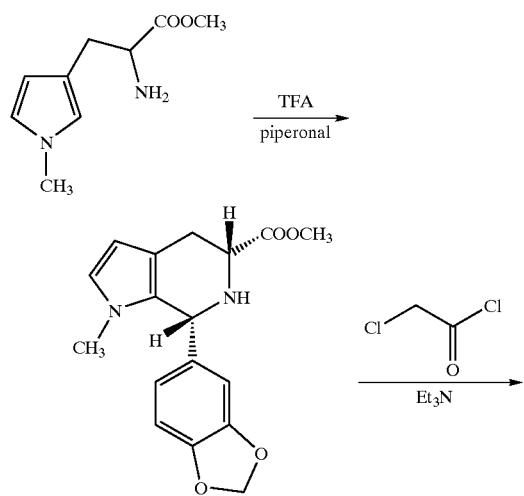

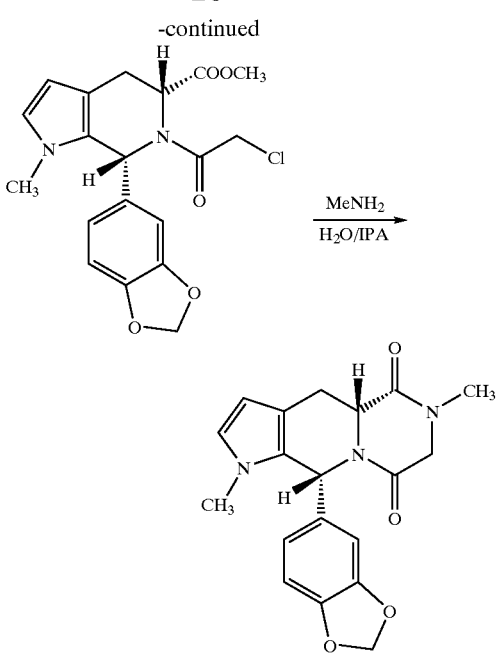

PREPARATION OF EXAMPLE 4 AND 5

Examples 4 and 5 can be prepared by the synthetic sequence of Example 3.

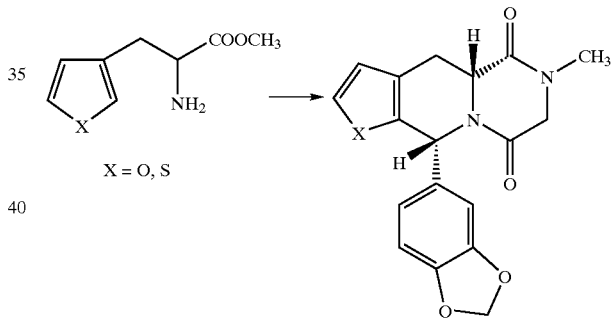

Example 4 (X = O)
Example 5 (X = S)

PREPARATION OF EXAMPLE 6

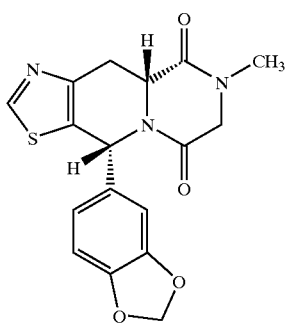

Example 6 can be prepared by the following synthetic sequence.

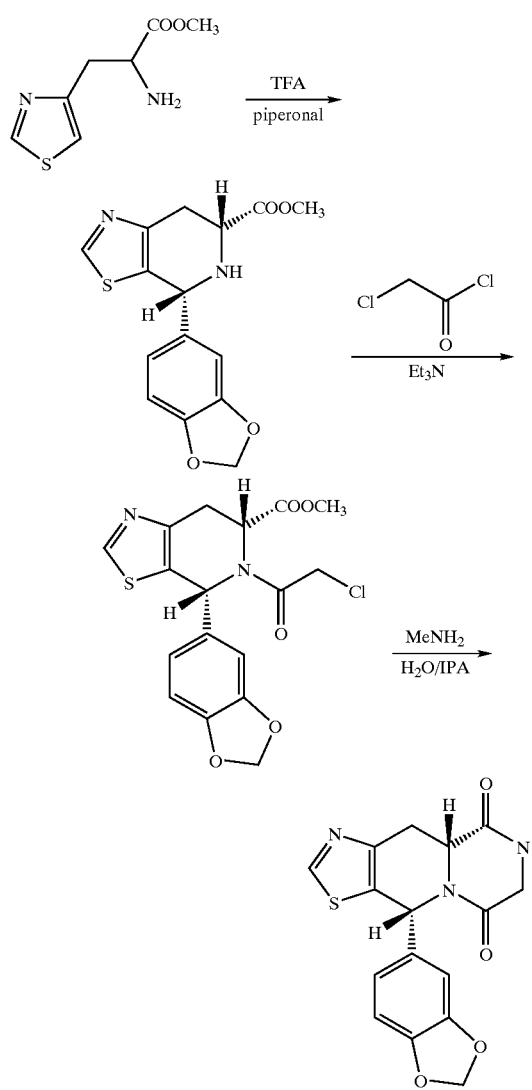
PREPARATION OF EXAMPLE 7
Example 7 can be prepared by the synthetic sequence of Example 6.
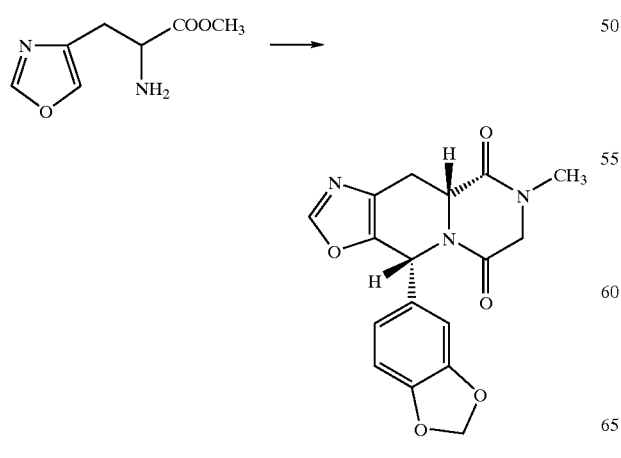
PREPARATION OF EXAMPLE 8
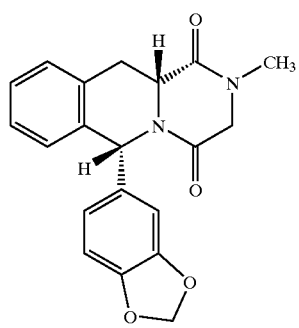
The compound of Example 8 can be prepared by the following synthetic sequence.
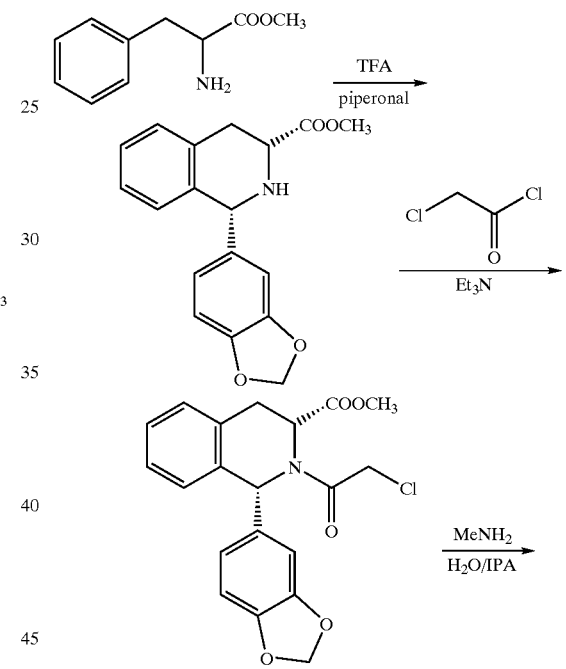
PREPARATION OF EXAMPLE 9
Example 9 can be prepared by the synthetic sequence of Example 8.

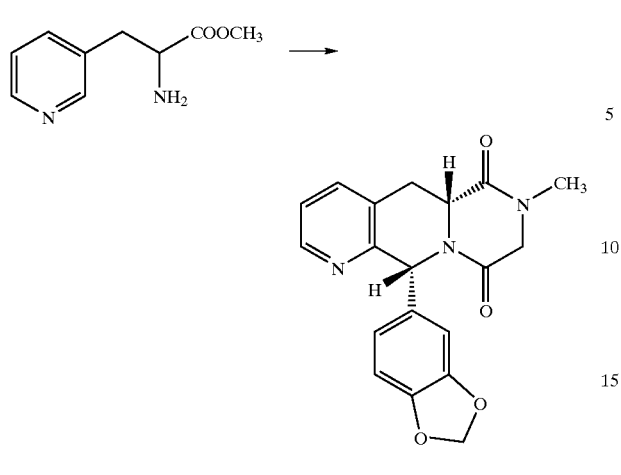

PREPARATION OF EXAMPLE 10
(6R,11aS)-6-Benzo[1,3]dioxol-5-yl-8,9-dimethoxy-2-methyl-2,3,11,11a-tetrahydro-6H-pyrazino-[[1,2-b]isoquinoline-1,4-dione

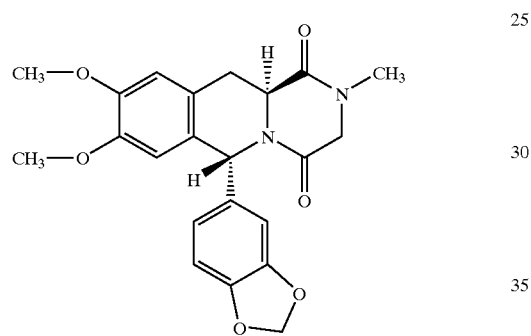

Tetrahydroisoquinoline analog Example 10 was prepared from 3-(3,4-dimethoxyphenyl)-L-alanine 1 as depicted in the following synthetic scheme. See, A. K. Saxena et al., *Indian J. Chem.*, 13, 230–237 (1975).

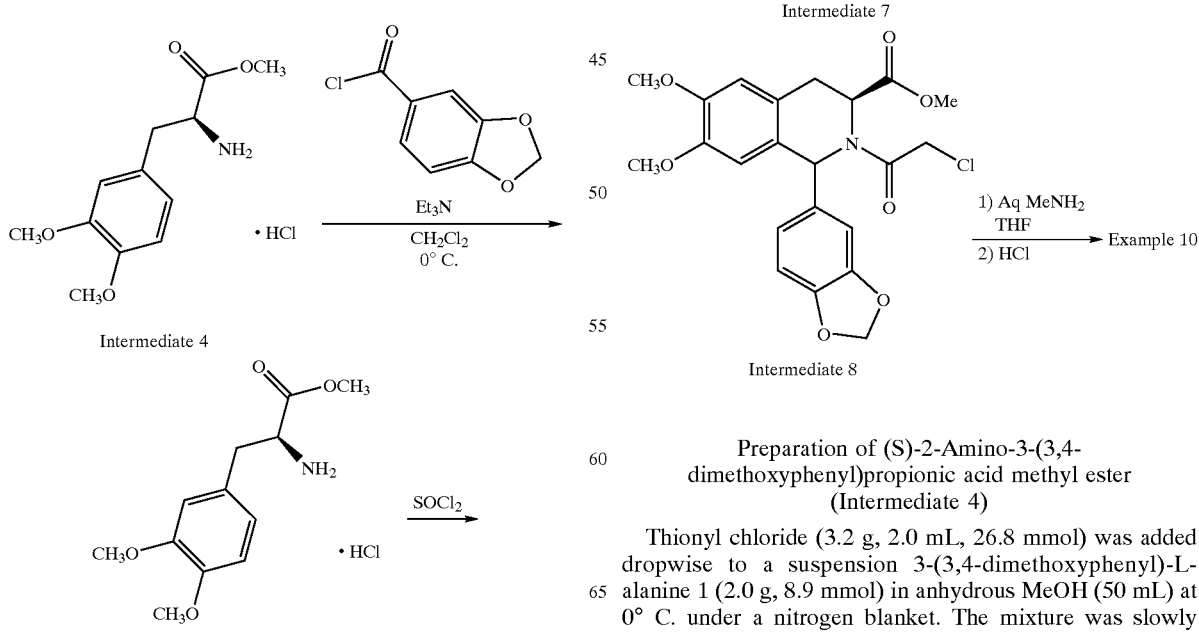

Preparation of (S)-2-Amino-3-(3,4-dimethoxyphenyl)propionic acid methyl ester (Intermediate 4)

Thionyl chloride (3.2 g, 2.0 mL, 26.8 mmol) was added dropwise to a suspension 3-(3,4-dimethoxyphenyl)-L-alanine 1 (2.0 g, 8.9 mmol) in anhydrous MeOH (50 mL) at 0° C. under a nitrogen blanket. The mixture was slowly warmed to room temperature, then stirred for 72 hours. The solvent was removed under reduced pressure to provide a solid. The crude product was taken up in CH$_2$Cl$_2$, then washed with saturated NaHCO$_3$ and saturated NaCl. The organic layer was dried over anhydrous Na$_2$SO$_4$, filtered and concentrated to yield a light brown oil (1.97 g, 93%).

Preparation of 2-(1-Benzo[1,3]dioxol-5-yl-methanoyl)amino]-3-(3,4-dimethoxyphenyl)-propionic acid methyl ester (Intermediate 5)

Piperonyloyl chloride (1.90 g, 2.14 mmol) was added portionwise to a mixture of crude Intermediate 4 (1.90 g, 7.94 mmol) and Et$_2$O (2.5 mL, 18.3 mmol) in CH$_2$Cl$_2$ (40 mL) at 0° C. under a nitrogen blanket. The resulting mixture was stirred for 4 hours at 0° C., then warmed to room temperature. The reaction was diluted with CH$_2$Cl$_2$ (50 mL) and was washed with 0.2 M HCl (2×40 mL), saturated NaHCO$_3$ (40 mL), and saturated NaCl (40 mL). The solution was dried over anhydrous Na$_2$SO$_4$, filtered, and concentration in vacuo to provide a white solid. The solid was collected by filtration and washed with 20% EtOAc/hexane to yield 3.69 g (100%) of Intermediate 5.

TLC R$_f$ (5% MeOH/CH$_2$Cl$_2$)=0.57; $^1$H NMR (300 MHz, CDCl$_3$): δ 8.62 (d, J=7.7 Hz, 1H), 7.42 (dd, J=1.7 Hz, J=8.13 Hz, 1H), 7.36 (d, J=1.6 Hz, 1H), 6.98 (d, J=8.2 Hz, 1H), 6.91 (d, J=1.7 Hz, 1H), 6.77–6.85 (m, 2H), 6.09 (s, 2H), 4.58 (m, 1H), 3.69 (s, 6H), 3.64 (s, 3H), 2.95–3.10 (m, 2H)

Preparation of 1-Benzo[1,3]dioxol-5-yl-6,7-dimethoxy-3,4,4a,-8a-tetrahydroisoquinoline-3-carboxylic acid methyl ester (Intermediate 6)

A mixture of Intermediate 5 (3.074 g, 7.94 mmol), and POCl$_3$ (15 mL) was heated at 120° C. under a nitrogen blanket for 1.5:hours. The mixture was cooled to room temperature, then poured onto ice water (100 mL) and extracted with EtOAc (2×200 mL). The combined organic layers were dried over anhydrous Na$_2$SO$_4$, filtered, and concentrated to a tan foam. The crude product was purified by column chromatography on silica gel using 1% Et$_3$N in 5% MeOH/CH$_2$Cl$_2$ to provide Intermediate 6 as a beige foam (1.60 g, 55%): TLC R$_f$ (5% MeOH/CH$_2$Cl$_2$)=0.55; $^1$H NMR (300 MHz, CDCl$_3$) δ: 7.17 (d, J=1.6 Hz, 1H), 7.11 (dd, J=8.0 Hz, J=1.6 Hz, 1H), 6.85 (m, 2H), 6.79 (s, 1H), 6.01 (d, J=1.1 Hz, 2H), 4.30 (dd, J=12.3 Hz, J=6.3 Hz, 1H), 3.95 (s, 3H), 3.81 (s, 3H), 3.77 (s, 3H), 2.91–3.08 (m, 2H); MS (API) m/z 370 (M+H).

Preparation of 1-Benzo[1,3]dioxol-5-yl-6,7-dimethoxy-1,2,3,4,4a,8a-hexahydroisoquinoline-3-carboxylic acid methyl ester (Intermediate 7)

A solution of Intermediate 6 (1.5 g, 4.06 mmol) in MeOH (60 mL) was cooled to 0° C. and stirred under a nitrogen blanket. Sodium borohydride (154 mg) was added, and the resulting mixture was stirred for 2 hours. The reaction mixture then was concentrated in vacuo, during which time a white solid precipitated. The solid was triturated with MeOH (20 mL), collected by filtration, and dried to give 0.82 g (54%) of Intermediate 7: TLC R$_f$ (90:10:1 CH$_2$Cl$_2$/EtOAc/MeOH)=0.33; $^1$H NMR (300 MHz, CDCl) δ: 6.84 (dd, J=7.8 Hz, J=1.6 Hz, 1H), 6.76–6.79 (m, 2H), 6.62 (s, 1H), 6.21 (s, 1H), 5.95 (dd, J=3.4 Hz, J=1.1 Hz, 2H), 5.02 (bs 1H), 3.82–3.86 (m, 1H), 3.86 (s, 3H), 3.78 (s, 3H) 3.64 (s, 3H), 3.01–3.14 (m, 2H), 2.41 (bs, NH); MS (API) m/z 372 (M+H).

Preparation of 1-Benzo[1,3]dioxol-5-yl-2-(2-chloroethanoyl)-6,7-dimethoxy-1,2,3,4,4a,8a-hexahydroisoquinoline-3-carboxylic acid methyl ester (Intermediate 8)

Chloroacetyl chloride (0.23 mL), 2.88 mmol) was added dropwise to a mixture of Intermediate 7 (0.82 g, 2.21 mmol) and Et$_3$N (0.71 mL, 5.09 mmol) in CH$_2$Cl$_2$ (15 mL) at 0° C. under a nitrogen blanket. The resulting mixture was warmed to room temperature and stirred for about 0.5 hour. The reaction was quenched with 1 N HCl (2 mL), and diluted with CH$_2$Cl$_2$ (50 mL) and-water (10 mL). The layers were separated and the organic was washed with saturated NaCl and dried over anhydrous Na$_2$SO$_4$. Filtration and concentration in vacuo afforded Intermediate 8 (1.5 g), which was used without further purification. TLC R$_f$ (10% EtOAc/CH$_2$Cl$_2$)=0.55; MS (API) m/z 448 (M+H), 472 (M+Na).

PREPARATION OF EXAMPLE 10

A mixture of crude Intermediate 8 (0.99 g, 2.21 mmol), 40% MeNH$_2$ in water (1.8 mL, 22.2 mmol) in THF (15 mL) was heated at 45° C. under a nitrogen blanket for 1.5 hours. The reaction was quenched with concentrated HCl until the pH was acidic. The mixture was concentrated to remove THF. To the resulting slurry was added 3:1 water:MeOH (30 mL) The solid was collected by filtration, washed with water and Et$_3$O (2×10 mL), and dried to provide Example 10 as a white solid (0.74 g, 82%): mp 235–236° C.; TLC R$_f$ (10% EtOAc/CH$_2$Cl$_2$)=0.14; $^1$H NMR (300 MHz, DMSO-d$_6$) δ: 7.21 (s, 1H), 6.99 (s, 1H), 6.74–6.77 (m, 2H), 6.54 (dd, J=1.2 Hz, J=7.4 Hz, 1H), 6.29 (a, 1H), 5.94 (d, J=6.3 Hz, 2H), 4.17–4.28 (m, 2H), 3.93 (d, J=16.5 Hz, 1H), 3.76 (s, 3H), 3.74 (s, 3H), 3.17 (dd, J=3.2 Hz, J=3.9 Hz, 1H), 2.95 (s 3H), 2.72 (dd, J=2.7 Hz, J=12.9 Hz, 1H); MS (API) m/z 411 (M+H), 433 (M+Na); [α]$_D^{25°\ C.}$=no observed rotation (c=0.43, DMSO). Anal. Calcd for C$_{22}$H$_{22}$N$_2$O$_6$e0.15H$_2$O: C, 6.3.96; H, 5.44; N, 6.78. Found: C, 63.88; H, 5.45; N, 6.84. The relative stereochemistry of the product was confirmed to be the trans isomer by NOE difference experiments (DMSO-d$_6$): no positive NOE enhancements from the C6 proton at 3.93 ppm to the C11 proton at 6.29 ppm.

PREPARATION OF EXAMPLE 11

The compound of Example 11 can be prepared by the synthetic sequence of Example 10.

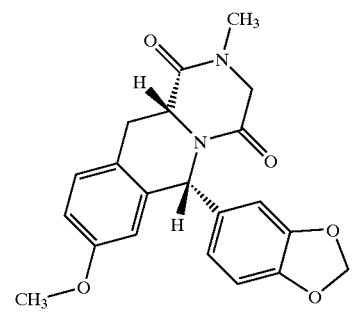

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion can be blended with excipients, then pressed into tablets, which optionally are film-coated.

The compounds of structural-formula (I) were tested for an ability to inhibit PDE5. The ability of a compound to inhibit PDE5 activity is related to the IC$_{50}$ value for the compound, i.e., the concentration of inhibitor required for 50% inhibition of enzyme activity. The IC$_{50}$ value for compounds of structural formula (I) were determined using recombinant human PDE5.

The compounds of the present invention typically exhibit an $IC_{50}$ value against recombinant human PDE5 of less than about 50 µM, and preferably less than about 25 µM, and more preferably less than about 15 µm. The compounds of the present invention typically exhibit an $IC_{50}$ value against recombinant human PDE5 of less than about 1 µM, and often less than about 0.05 µM. To achieve the full advantage of the present invention, a present PDE5 inhibitor has an $IC_{50}$ of about 0.1 nM to about 15 µM.

The production of recombinant human PDEs and the $IC_{50}$ determinations can be accomplished by well-known methods in the art. Exemplary methods are described as follows:

Expression of Human PDEs

Expression in *Saccharomyces Cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector-employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 µL reaction mixture containing (final concentrations) 40 µM Tris HCl (pH 8.0), 1 µM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) µg of Crotalus atrox venom then was added, and the incubation was continued for 3 minutes (15 minutes total). The reaction was stopped by addition of 200 µL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 µM $ZnSO_4$). Cells-were lysed in a Microfluidizer® (Microfluidics Corp.) using nitrogen at 20,000 psi. The lysate was centrifuged and filtered through 0.45 µm disposable filters. The filtrate was applied to a 150 mL column of Q SEPHAROSE® Fast-Flow (Pharmacia). The column was washed with 1.5 volumes of Buffer A (20 nM Bis-Tris Propane, pH 6.8, 1 mM $MgCl_2$, 0.25 mM DTT, 10 µM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 µM $ZnS_4O$, and 0.250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 µM $ZnSO_4$). The pool was applied to/a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 µmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 µg/ml 5'-Nucleotidase, 1 mM EGTA, and 0.15 µM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes-during which the total substrate conversion did not exceed 30%.

The $IC_{50}$ values for the compounds examined were determined from concentration-response curves typically using concentrations ranging from 10 nM to 10 µM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 1000 nM. An in vitro test data for representative compounds of the invention is given in the following table:

TABLE 1

| In vitro results | |
|---|---|
| Example | PDE5 $IC_{50}$ (nM) |
| 1 | 3240 |
| 10 | 718 |

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

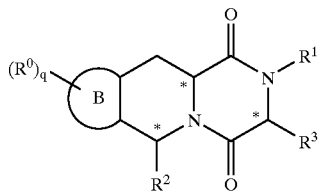

wherein $R^0$, independently, is selected from the group consisting of halo, $C_{1-6}$alkyl, $C_{2-6}$alkenyl, aryl, heteroaryl, $C_{3-8}$cycloalkyl, $C_{3-8}$heterocycloalkyl, $C_{1-3}$alkylenearyl, $C_{1-3}$alkyleneheteroaryl, Het, C(=O)$R^a$, OC(=O)O$R^a$, $C_{1-4}$alkyleneN$R^aR^b$, $C_{1-4}$alkyleneHet, $C_{1-4}$alkyleneC(=O)ORa, C(=O)NR$^a$SO$_2$R$^b$, C(=O)C$_{1-4}$alkyleneHet, C(=O)NRaRb, C(=O)NR$^a$C$_{1-4}$alkyleneOR$^b$, C(=O)NR$^a$C$_{1-4}$alkyleneHet, OR$^a$, OC$_{1-4}$alkyleneC(=O)OR$^a$, OC$_{1-4}$alkyleneNR$^a$R$^b$, OC$_{1-4}$alkyleneHet, OC$_{1-4}$alkyleneOR$^a$, OC$_{1-4}$alkyleneNR$^a$C(=O)OR$^b$, NR$^a$R$^b$, NR$^a$C$_{1-4}$alkyleneNR$^a$R$^b$, NR$^a$C(=O)R$^b$, NR$^a$C(=O)NR$^a$R$^b$, N(SO$_2$C$_{1-4}$alkyl)$_2$, NR$^a$(SO$_2$C$_{1-4}$alkyl), nitro, trifluoromethyl, trifluoromethoxy, cyano, SO$_2$NR$^a$R$^b$, SO$_2$R$^a$, SOR$^a$, SR$^a$, and OSO$_2$CF$_3$;

$R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkylC$_{1-3}$alkyl, arylC$_{1-3}$alkyl, and heteroarylC$_{1-3}$alkyl;

$R^2$ is selected from the group consisting of an optionally substituted monocyclic aromatic ring selected from the group consisting of benzene, thiophene, furan, and pyridine, and an optionally substituted bicyclic ring

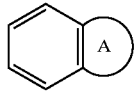

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is hydrogen or $C_{1-6}$alkyl, or $R^1$ and $R^3$ together form a 3- or 4-membered alkyl or alkenyl chain component of a 5- or 6-membered ring;

fused ring B is a 5-, 6-, or 7-membered ring, saturated or partially or fully unsaturated, comprising carbon atoms and optionally one to three heteroatoms selected from oxygen, sulfur, and nitrogen;

$R^a$ is selected from the group consisting of hydrogen, $C_{1-10}$alkyl, $C_{2-10}$alkenyl, $C_{2-10}$alkynyl, aryl, heteroaryl, arylC$_{1-3}$alkyl, $C_{1-3}$alkylenearyl, C(=O)OR$^b$, C(=O)N(R$^b$)$_2$, $C_{1-4}$alkyleneN(R$^b$)$_2$, halo, NO$_2$, CF$_3$, CF$_3$O, OR$^b$, OC(=O)R$^b$, OC$_{1-4}$alkyleneC(=O)OR$^b$, $C_{1-4}$alkyleneOC$_{1-4}$alkyleneC(=O)OR$^b$, C(=O)NR$^b$SO$_2$R$^b$, C(=O)C$_{1-4}$alkyleneHet, C$_{2-6}$alkenyleneN(R$^b$)$_2$, C(=O)NR$^b$C$_{1-4}$alkyleneOR$^b$, C(=O)NR$^b$C$_{1-4}$alkyleneHet, OC$_{2-4}$alkyleneN(R$^b$)$_2$, OC$_{1-4}$alkyleneCH(OR$^b$)CH$_2$N(R$^b$)$_2$, OC$_2$alkyleneOR$^b$, OC$_{2-4}$alkyleneNR$^b$C(=O)OR$^b$, N(R$^b$)$_2$, NR$^b$C$_{1-4}$alkyleneN(R$^b$)$_2$, NR$^b$C(=O)R$^b$, NR$^b$C(=O)N(R$^b$)$_2$, N(SO$_2$C$_{1-4}$alkyl)$_2$, NR$^b$(SO$_2$C$_{1-4}$alkyl), SO$_2$N(R$^b$)$_2$, OSO$_2$trifluoromethyl, C(=O)R$^b$, C$_{1-3}$alkyleneOR$^b$, CN, and C$_{1-6}$alkyleneC(=O)OR$^b$;

$R^b$ is selected from the group consisting of hydrogen $C_{1-6}$alkyl, aryl, arylC$_{1-3}$alkyl, C$_1$alkylenearyl, heteroaryl, heteroarylC$_{1-3}$alkyl, and $C_{1-3}$alkyleneheteroaryl;

q is 0, 1, 2, 3, or 4; or a pharmaceutically acceptable salt or a hydrate thereof.

2. The compound of claim 1 represented by the formula

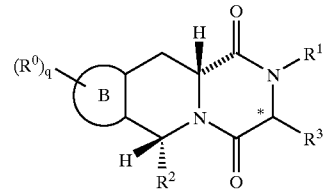

or a pharmaceutically acceptable salt or a hydrate thereof.

3. The compound of claim 1 wherein q is 0.

4. The compound of claim 1 wherein $R^0$ is selected from the group consisting of $C_{1-6}$alkyl, aryl, $C_{1-3}$alkylenearyl, $C_{1-3}$alkyleneheteroaryl, Het, OR$^a$, C(=O)OR$^a$, $C_{1-4}$alkyleneNR$^aR^b$, C(=O)R$^a$, NR$^aR^b$, $C_{3-}$cycloalkyl, and C(=O)NR$^aR^b$.

5. The compound of claim 1 wherein $R^1$ is selected from the group consisting of hydrogen, $C_{1-6}$alkyl, halo$C_{1-6}$alkyl, $C_{3-8}$cycloalkyl, $C_{3-}$cycloalkyleneC$_{1-3}$alkyl, arylC$_{2-3}$alkyl, and heteroarylC$_{1-3}$alkyl.

6. The compound of claim 1 wherein $R^2$ is an optionally substituted bicyclic ring selected from the group consisting of naphthalene, indene, benzoxazole, benzothiazole, benzisoxazole, benzimidazole, quinoline, indole, benzothiophene, and benzofuran.

7. The compound of claim 1

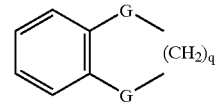

and wherein q is an integer 1 or 2, and G, independently, are C(R$^a$)2, O, S, or NR$^a$.

8. The compound of claim 1 wherein $R^2$, substituted or unsubstituted, is selected from the group consisting of

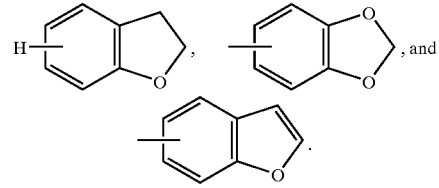

9. The compound of claim 1 wherein the B ring is selected from the group consisting of cyclopentyl, cyclohexyl, cycloheptyl, cyclopentenyl, cyclohexenyl, 1,3,5-cyclohepatrienyl, phenyl, furanyl, thienyl, 2H-pyrrolyl, pyrrolyl, 2-pyrrolinyl, 3-pyrrolinyl, pyrrolidinyl, 1,3-dioxolanyl, oxazolyl, thiazolyl, imidazolyl, 2-imidazolinyl, imidazolidinyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, 3H-pyrrolyl, 1,2-dithiolyl, 1,3-dithiolyl, 3H-1,2-oxathiolyl, 1,2,4-oxadiazolyl, 1,2,5-oxadiazolyl, 1,3,4-oxadiazolyl, 1,2,3,4-oxatriazolyl, 1,2,3,5-oxatriazolyl, 3H-1,2,3-dioxazolyl, 1,2,4-dioxazole, 1,3,2-dioxazole, 1,3,4-dioxazolyl, 5H-1,2,5-oxathiazolyl, 1,3-oxathiolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,3,5-trithanyl, 2-pyrronyl, 4-pyronyl, 1,2-dioxinyl, 1,3-dioxinyl, 1,2,4-triazinyl, 1,2,3-triazinyl, 4H-1, 3-oxadinyl, 2H-1,3-oxazinyl, 6H-1,3-oxazinyl, 6H-1,2-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2, 5-oxathiazinyl, 1,2,6-oxathiazinyl, 1,4,2-oxadiazinyl, 1,3,5, 2-oxadiazinyl, azepinyl, oxepinyl, thiepinyl, and 1,2,4-diazepinyl.

10. The compound of claim 9 wherein the B ring, unsubstituted or substituted, is selected from the group consisting of phenyl, imidazolyl, pyrrolyl, thienyl, furanyl, thiazolyl, oxazolyl, piperidinyl, cyclohexyl, pyrimidinyl, triazinyl, piperazinyl, and imidazolinyl.

11. A compound selected from the group consisting of

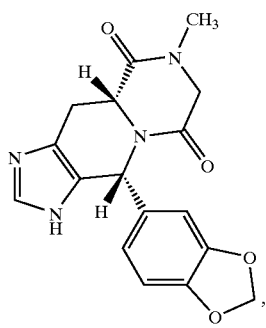

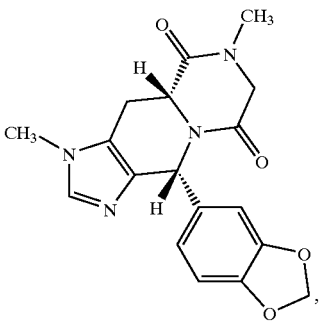

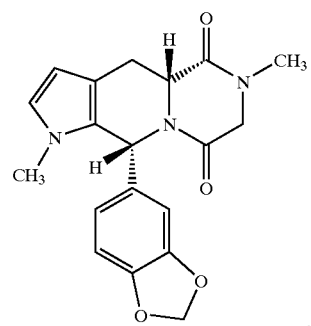

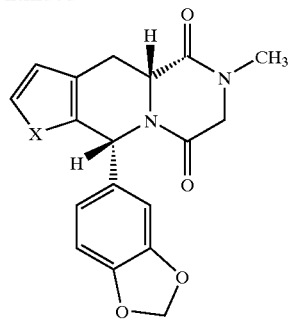

wherein X = O or S

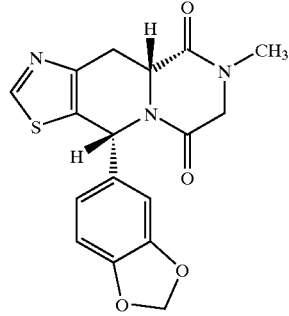

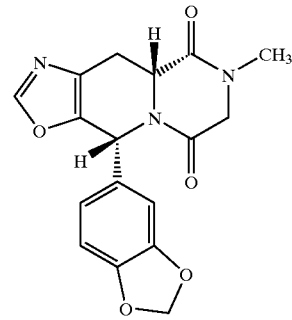

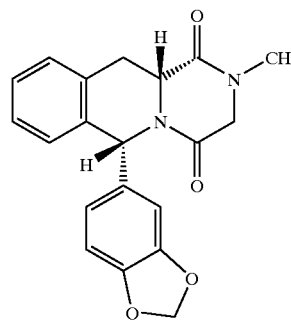

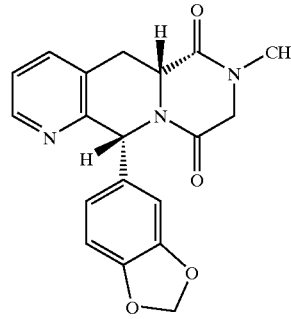

-continued

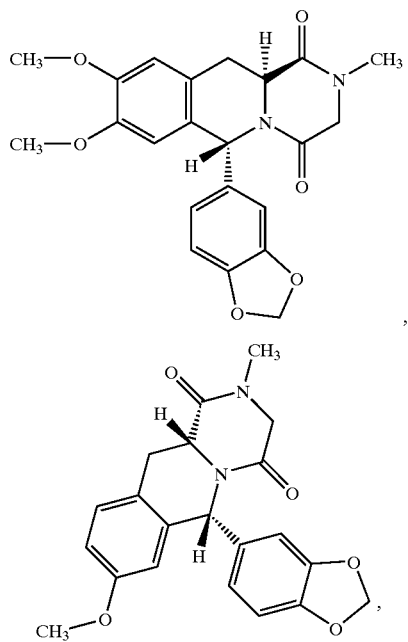

, or a pharmaceutically acceptable salt or a hydrate thereof.

12. A pharmaceutical composition comprising a compound of claim 1, together with a pharmaceutically acceptable diluent or carrier.

13. A method of treating a male animal for male erectile dysfunction or a female animal for female arousal disorder comprising administering to said animal with an effective amount of a pharmaceutical composition comprising a compound of claim 1, together with a pharmaceutically acceptable diluent or carrier.

14. The method of claim 13 wherein the condition is male erectile dysfunction.

15. The method of claim 13 wherein the condition is female arousal disorder.

16. The method of claim 14 wherein the treatment is an oral treatment.

17. The method of claim 15 wherein the treatment is an oral treatment.

18. A method of treating hypertension in a human or a nonhuman animal body, comprising administering to said body a therapeutically effective amount of a compound of claim 1.

19. The method of claim 18 wherein the hypertension is pulmonary hypertension, or malignant hypertension.

20. A method for the treatment of male erectile dysfunction or female arousal disorder, comprising administration of an effective dose of a compound of claim 1, or a pharmaceutically acceptable salt or a hydrate thereof, to the male or female.

* * * * *

UNITED STATES PATENT AND TRADEMARK OFFICE
CERTIFICATE OF CORRECTION

PATENT NO. : 6,960,587 B2  Page 1 of 3
APPLICATION NO. : 10/398819
DATED : November 1, 2005
INVENTOR(S) : Mark W. Orme et al.

It is certified that error appears in the above-identified patent and that said Letters Patent is hereby corrected as shown below:

Column 1, line 40, "$C_{1-3}$-alkylenearyl" should be -- $C_{1-3}$alkylenearyl --

Column 1, line 44, "$C(=O)NR^{a}C_{3-4}$ . . ." should be -- $C(=O)NR^{a}C_{1-4}$ . . .--

Column 1, line 54, "aryl $C_{1-3}$alkyl" should be -- aryl$C_{1-3}$alkyl --

Column 2, line 14, "$OC(=O)-R^{b}$" should be -- $OC(=O)R^{b}$ --

Column 2, line 18, "$OC_{1-4}$alkyleneCH($OR^{b}$) -CH2N $(R^{b})_2$" should be
-- $OC_{1-4}$alkyleneCH $(OR^{b})$ $CH_2N$ $(R^{b})_2$ --

Column 2, line 20, "$NR^{b}C(=O) -N(R^{b})_2$" should read -- $NR^{b}C(=O)$ N $(R^{b})_2$ --

Column 2, line 26, "alkyl" should be -- alkyl --

Column 3, line 30, "hydroxyl" should be -- hydroxy --

Column 3, line 31, "alkoxyl" should be -- alkoxy --

Column 3, line 35, "(alkylthio)-alkyl" should be -- (alkylthio) alkyl --

Column 3, line 53, delete the comma after "trifluoromethyl,"

Column 3, line 60, "$C_{1-4}$alkylene-$NR^{a}R^{b}$" should be -- $C_{1-4}$alkylene$NR^{a}R^{b}$ --

Column 9, line 33, "formula, (I)" should be -- formula (I) --

Column 11, line 24, "lactose.," should be -- lactose, --

Column 11, line 46, "the-present" should be -- the present --

Column 12, in structure labeled (IV), "$(R_0)_q$" should be -- $(R^{0})_1$ --

Column 16, line 44, "tetraaza-cyclopenta" should be -- tetraazacyclopenta --

Column 18, line 19, "(m, 2H)" should be -- (m, 2H): --

Column 18, line 21, "0.10%" should be -- 10% --
    "MeOH/ -$CH_2Cl_2$" should be -- MeOH/$CH_2Cl_2$ --

UNITED STATES PATENT AND TRADEMARK OFFICE
CERTIFICATE OF CORRECTION

PATENT NO. : 6,960,587 B2
APPLICATION NO. : 10/398819
DATED : November 1, 2005
INVENTOR(S) : Mark W. Orme et al.

It is certified that error appears in the above-identified patent and that said Letters Patent is hereby corrected as shown below:

Column 18, line 35, "MeOH/ -CH$_2$Cl$_2$" should be -- MeOH/CH$_2$Cl$_2$ --

Column 18, line 37, "(M+H)" should be -- (M+H) . --

Column 18, line 62, "C$_{17}$H$_{17}$N$_4$O$_4$.HCl.0.4H$_2$O" should be -- C$_{17}$H$_{17}$N$_4$O$_4$•HCl•0.4 H$_2$O --

Column 18, line 66, "C$_4$" should be -- C4 --

Column 21, line 47, "Example ?" should be -- Examine 7 --

Column 23, line 23, "[ [l,2-b]" should be -- [l,2-b] --

Column 25, line 6, "2-(1-Benzo) . . ." should be -- 2-[ (l-Benzo) . . . --

Column 25, line 25, " (m, 2H) " should be -- (m, 2H) . --

Column 25, line 27, ". . .3,4,4a,-8a– . . ." should be -- . . .3,4,4a,8a-. . . --

Column 25, line 31, "1.5: hours" should be -- 1.5 hours --

Column 25, line 55, "CDCl" should be --CDCl$_3$ --

Column 26, line 19, "(30mL)" should be -- (30mL) . --

Column 26, line 24, "6.29 (a, 1H)," should be -- 6.29 (s, 1H), --

Column 26, line 26, "2.95 (s 3H)," should be -- 2.95 (s, 3H), --

Column 26, line 30, "6.3.96;" should be -- 63.96; --

Column 26, line 61, delete the hyphen between "structural" and "formula"

Column 27, line 19, delete the hyphen between "vector" and "employed"

Column 27, line 27, "2xSC-leu" should be -- 2X SC-leu --

Column 27, line 30, "2xYET/3%" should be -- 2X YET/3% --

UNITED STATES PATENT AND TRADEMARK OFFICE
CERTIFICATE OF CORRECTION

PATENT NO.         : 6,960,587 B2
APPLICATION NO. : 10/398819
DATED                  : November 1, 2005
INVENTOR(S)        : Mark W. Orme et al.

It is certified that error appears in the above-identified patent and that said Letters Patent is hereby corrected as shown below:

Column 27, line 64, delete hyphen between "Cells" and "were"

Column 28, line 2, "20 nM" should be -- 20 mM --

Column 28, line 10, "ZnS$_4$O" should be -- ZnSO$_4$ --

Column 28, line 10, "0.250 mM" should be -- 250 mM --

Column 28, line 16, delete slash between "to" and "a"

Column 28, line 38, delete hyphen between "minutes" and "during"

Column 30, line 36, insert -- wherein $R^2$ is -- after "claim 1"

Column 30, claim 8, first structure,

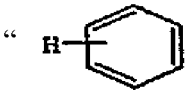  should be --  --

Signed and Sealed this

Second Day of January, 2007

JON W. DUDAS
*Director of the United States Patent and Trademark Office*